(12) United States Patent
Alur et al.

(10) Patent No.: US 8,691,278 B2
(45) Date of Patent: *Apr. 8, 2014

(54) SELF SOLIDIFYING BIOERODIBLE BARRIER IMPLANT

(71) Applicant: TriLobic Pharma LLC, Tallassee, AL (US)

(72) Inventors: Hemant H. Alur, Haskell, NJ (US); James A. H. Harwick, Tallassee, AL (US); Pravakar Mondal, Kansas City, MO (US); Thomas P. Johnston, Overland Park, KS (US)

(73) Assignee: Trilogic Pharma LLC, Tallassee, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/940,630

(22) Filed: Jul. 12, 2013

(65) Prior Publication Data

US 2013/0338088 A1   Dec. 19, 2013

Related U.S. Application Data

(63) Continuation of application No. 12/740,548, filed as application No. PCT/US2008/085259 on Dec. 2, 2008, now Pat. No. 8,501,230.

(60) Provisional application No. 60/991,903, filed on Dec. 3, 2007.

(51) Int. Cl.
*A61K 9/14* (2006.01)

(52) U.S. Cl.
USPC .......................................................... 424/486

(58) Field of Classification Search
None
See application file for complete search history.

*Primary Examiner* — Paul Dickinson
(74) *Attorney, Agent, or Firm* — Clark G. Sullivan; Troutman Sanders LLP

(57) ABSTRACT

Provided are bioerodible compositions that can be implanted into cavities or mammalian tissue as a liquid or semi-liquid and which solidify upon exposure of the body temperature of the mammal. The implants erode over a prescribed period of time and elute a drug. The implants also form a seal with the skin or mucosa surrounding the cavity to prevent the entry of bacterial pathogens.

22 Claims, 4 Drawing Sheets

SELF SOLIDIFYING BIOERODIBLE BARRIER IMPLANT

RELATIONSHIP TO PRIOR APPLICATIONS

This application is a continuation of pending prior application U.S. Ser. No. 12/740,548 filed Apr. 29, 2013, which was a 371 filing of PCT application PCT/US08/085259 filed Dec. 2, 2008, which claims priority to U.S. Provisional Application No. 60/991,903 filed Dec. 3, 2007, the contents of which are hereby incorporated in their entirety by reference.

FIELD OF THE INVENTION

The present invention is in the field of bioerodible implants that are implanted into open cavities of human tissue including periodontal pockets, surgical incisions, and open wounds. The invention relates particularly to bioerodible implants that are drug eluting, and that act as a barrier when implanted against infiltration by exogenous pathogens.

BACKGROUND OF THE INVENTION

Biodegradable polymers are a large and growing segment of the medical device market, and have found varying applications for use. They are predominantly used in sutures, but have also found use in orthopedic fixation devices such as interference screws in the ankle, knee, and hand areas; as tacks and pins for ligament attachment and meniscal repair; as suture anchors; and as rods and pins for fracture fixation.

Biodegradable polymers have also found use in at least two dental applications. Employed as a void filler following tooth extraction, porous polymer particles can be packed into the cavity to aid in quicker healing. As a guided-tissue-regeneration (GTR) membrane, films of biodegradable polymer can be positioned to exclude epithelial migration following periodontal surgery. The exclusion of epithelial cells allows the supporting, slower-growing tissue—including connective and ligament cells—to proliferate. Three examples of these GTR materials are Resolut™ from W. L. Gore (Flagstaff, Ariz.) (a poly(dl-lactide-co-glycolide) (PGA-DLPLA) polymer), Atrisorb™ from Atrix Laboratories (Fort Collins, Colo.) (a poly(dl-lactide) (DLPLA) polymer) and Vicryl™ mesh from Ethicon (a poly(l-lactide-co-glycolide) (PGA-LPLA) polymer).

Poloxamers and their use have a long history. Chemically, they are non-ionic, triblock copolymers of the following general structure:

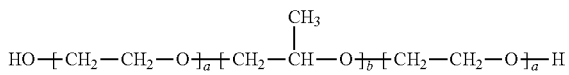

The structure consists of a hydrophobic central core of propylene oxide (represented by "b" in the above figure), flanked by hydrophilic ethylene oxide (represented by "a" in the above figure) on both sides. Poloxamers are soluble in water and other polar and non-polar solvents and are regarded as chemically inert. Commercially, poloxamers are available from BASF as flakes (denoted by "F"), paste (denoted by "P"), liquid (denoted by "L") and micronized (denoted by "micro"). Their chemical composition and specifications are provided below in Tables 1 and 2.

TABLE 1

| Pluronic ® | Poloxamer | a | b | Content of Oxyethylene (Percent) | Molecular Weight |
|---|---|---|---|---|---|
| L 44 NF | 124 | 12 | 20 | 44.8-48.6 | 2090-2360 |
| F 68 NF | 188 | 80 | 27 | 79.9-83.7 | 7680-9510 |
| F 87 NF | 237 | 64 | 37 | 70.5-74.3 | 6840-8830 |
| F 108 NF | 338 | 141 | 44 | 81.4-84.9 | 12700-17400 |
| F 127 NF | 407 | 101 | 56 | 71.5-74.9 | 9840-14600 |

TABLE 2

| | Poloxamer | | | | |
|---|---|---|---|---|---|
| | 124 | 188 | 237 | 338 | 407 |
| Physical Form | Liquid | Solid | Solid | Solid | Solid |
| pH (2.5% in water) | 5.0-7.5 | 5.0-7.5 | 5.0-7.5 | 5.0-7.5 | 5.0-7.5 |
| Cloud point, 10% | 71-75° C. | >100° C. | >100° C. | >100° C. | >100° C. |
| APHA color | 50 max. | 100 max. | 100 max. | 100 max. | 120 max. |
| % $H_2O$ | 0.4 max. | Cast solid 0.4 max. Prill 0.75 max. | Cast solid 0.4 max. Prill 0.75 max. | Cast solid 0.4 max. Prill 0.75 max. | Cast solid 0.4 max. Prill 0.75 max. |
| BHT, ppm | — | 50-125 | 50-125 | 50-125 | 50-125 |
| Unsaturation mEq/g | 0.020 ± 0.008 | 0.026 ± 0.008 | 0.034 ± 0.008 | 0.031 ± 0.008 | 0.048 ± 0.017 |
| Ethylene Oxide, ppm | 1 max. | 1 max. | 1 max. | 1 max. | 1 max. |
| Propylene Oxide, ppm | 5 max. | 5 max. | 5 max. | 5 max. | 5 max. |
| 1,4 dioxane, ppm | 0.002% max. | 0.002% max. | 0.002% max. | 0.002% max. | 0.002% max. |

Poloxamers show temperature dependent thermoreversible properties. Poloxamer 407 (F127) is the most well studied poloxamer for this behavior. Generally, this behavior has been studied in 20-30% w/w aqueous solutions, which are liquid at low temperature (2-5° C.) and turn into gel at room temperature (22-25° C.). This gelation temperature is dependent on the molecular weight and the percentage of the hydrophobic portion, hence the gelling temperature decreases as both the molecular weight and the hydrophobic fraction increases. In general, the gelation temperature increases in the order of F127<F108<F87<F68<F44. The gelation temperature can also be modulated by varying the percentage of F127, or mixing it with one or more other poloxamers. The three pharmaceutically relevant (due to availability and approved for use in pharmaceutical products) poloxamers are F127, F108, and F68.

Despite all of their interesting and useful physical properties, poloxamer gelled matrices have not been developed that can serve as a drug eluting implant, and that meet demanding requirements such as controlled drug release, controlled erosion, metabolic clearance, viscosity at room temperature, and adhesion to biological surfaces. The aim of this work was to develop a poloxamer formulation that could meet these demanding requirements, and function as a completely biocompatible and bioerodible drug delivery implant.

SUMMARY OF THE INVENTION

The inventors have surprisingly discovered a synergistic relationship between xanthan gum and a particular class of poloxamers, which allows this class of poloxamers to be used for the first time as self-solidifying drug-eluting bioerodible implants. The liquid exists at a viscosity that can be easily injected into a body cavity, and, subsequently, remains in place for the liquid to solidify. The implants which result from the injection disintegrate in adjacent aqueous-based extracellular fluids at a predictable rate over an extended period of time, elute active ingredient at a controlled rate, provide a barrier against entry of infectious pathogens, and are completely cleared and excreted from the body via normal pathways of elimination.

In a preferred embodiment, the composition is a liquid that comprises (a) from 70 to 90 weight parts water; (b) from 10 to 25 weight parts of a copolymer having the following block structure:

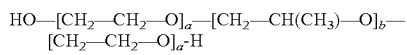

$$\mathrm{HO-[CH_2-CH_2-O]}_a\mathrm{-[CH_2-CH(CH_3)-O]}_b\mathrm{-[CH_2-CH_2-O]}_a\mathrm{-H}$$

wherein the ratio of a:b is from 1:1 to 3:1, and the molecular weight of said copolymer is from 9000 to 16000; and (c) from 1.0 to 3.0 weight parts of xanthan gum. The product can be injected into the dental sulci, or implanted at the site of a surgical incision or open wound before the incision or wound is sutured together. The implant preferably includes antibiotics that are eluted to surrounding tissue, while at the same time acting as a barrier to prevent further entry of pathogens into the sulci, incision or wound. The method is performed with a liquid composition that does four important things:

(1) The liquid converts to a solid or semi-solid gel in situ when injected into the sulci, incision or wound cavity, and penetrates into any crevices located within the cavity;

(2) The liquid contains a drug, preferably an antibiotic that is eluted over time from the implant onto the surfaces inside the cavity, and that eliminates any infection from bacteria that might otherwise invade the cavity;

(3) The implant is bioadhesive, and seals the skin or mucosa together from within the cavity, to form a bather against further bacterial invasion;

(4) The implant is bioerodible, so that it dissolves or disintegrates in adjacent extracellular fluids over time and is cleared from the implant site by normal elimination pathways.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Definitions and Use of Terms

Figure 1:
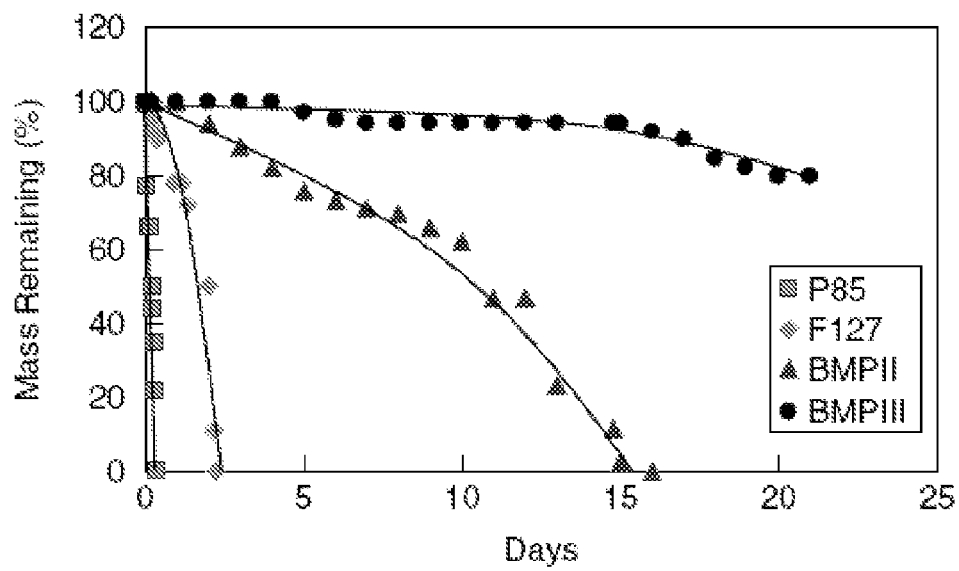
FIG. 1 presents a comparison of the erosion rates for poloxamers (P85 and F127) and BMPs of P85, wherein the initial concentration used to prepare the gel was 30%, as described in POLYM. INT. 54:842-847 (2005).

As used in this specification and in the claims, which follow, the singular forms "a," "an" and "the" include plural referents unless the context clearly dictates otherwise. Thus, for example, reference to "an ingredient" includes mixtures of ingredients; reference to "an active pharmaceutical agent" includes more than one active pharmaceutical agent, and the like.

"Pharmaceutically acceptable" means that which is useful in preparing a pharmaceutical composition that is generally safe, non-toxic and neither biologically nor otherwise undesirable and includes that which is acceptable for human pharmaceutical use.

"Therapeutically effective amount" means that amount which, when administered to an animal for treating or preventing a disease, is sufficient to effect such treatment or prevention for the disease.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the pharmaceutical industry and inherent in pharmaceutical products, such as differences in product strength due to manufacturing variation and time-induced product degradation. The term allows for any variation, which in the practice of pharmaceuticals would allow the product being evaluated to be considered bioequivalent in humans to the recited strength of a claimed product.

Xanthan gum refers to a high molecular weight polysaccharide used as a food additive and rheology modifier. It may be produced by a process involving fermentation of glucose or sucrose by the *Xanthomonas campestris* bacterium. The backbone of the polysaccharide chain consists of two β-D-glucose units linked through the 1 and 4 positions. The side chain consists of two mannose and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. Two of these chains may be aligned to form a double helix, giving a rather rigid rod configuration that accounts for its high efficiency as a viscosifier of water. The molecular weight of xanthan varies from about one million to 50 million depending upon how it is prepared. In a preferred embodiment for the current invention, the molecular weight of the xanthan ranges from approximately 1 to 25 million. In alternative embodiments, the molecular weight is 1, 2, 3, 4, or 5±0.5, or 6, 7, 8, 9, 10, 11, 12, 13, 14, 15, 16, 17, 18, 19, 19, 20, 21, 22, 23, 24, or 25±2.

Discussion

In one embodiment the invention provides a method for locally delivering a drug, particularly for preventing bacterial infections in the dental sulci, a surgical incision or open wound comprising: (a) providing a liquid characterized by: (i) a capacity to self-gel or self-solidify when contacted with mammalian tissue; (ii) an antibacterial effective amount of an antibiotic, or a therapeutically effective amount of another desired drug; (iii) a capacity to bioerode and elute said antibiotic or other drug when implanted in mammalian tissue; and (iv) a capacity to adhere to mammalian tissue at or below the surface of the skin or mucosa; (b) providing dental sulci, a surgical incision or an open wound in mammalian tissue, that defines a cavity, comprising exposed tissue below the mucosal surface or stratum corneum; (c) implanting said liquid into said cavity, (d) forming a barrier against pathogen entry into said cavity by implanting said liquid into said cavity, whereupon said liquid solidifies into a solid or semi-solid state in the form of an implant and adheres to said tissue around the entire periphery of said sulci, incision or wound; and (d) optionally closing said surgical incision or wound.

The liquid is preferably free or mass flowing, so that it may be administered through a syringe with a needle or other suitable device. A suitable syringe volume may preferably range from from 1 to 25 millimeters, and be injected using a needle ranging from 16 to 25 gauge. The incision or wound can be closed by any suitable mechanical structure, such as sutures, adhesive strips, or biocompatible glue. In a preferred embodiment, the barrier forming implant has a high degree of cohesiveness to said tissue surrounding said sulci, incision or wound, and said sulci, incision or wound is closed by the barrier forming implant.

In one embodiment, the cavity is defined by the dental sulci, and said implant remains in the sulci for a period of 5 to 21 days. In another embodiment, the liquid comprises an antibiotic, and a therapeutically effective amount of said antibiotic is released from said implant from 5 to about 21 days, or from 7 to 15 days. In still another embodiment, the liquid comprises an analgesic, further releasing a therapeutically effective amount of said analgesic from said implant from 1 to 21 days, or 1 to 5 days.

The liquid preferably employs polymeric chemistry to self-solidify. Polymers for practicing the invention can be either natural or synthetic. In general, synthetic polymers offer greater advantages than natural materials because they can be tailored to give a wider range of properties and more predictable lot-to-lot uniformity than can materials from natural sources. Synthetic polymers also represent a more reliable source of raw materials, one free from concerns of immunogenicity.

The general process for selecting a polymer for use as a biomaterial is to match the mechanical properties and the time of degradation to the needs of the application. This invention also imposes three additional demands on the polymer selected: the polymer must self-harden to a solid or semi-solid state when implanted into a body cavity; the polymer must elute drug at a suitable rate of release; and the polymer must form a barrier against entry of pathogens into the cavity.

Factors that affect the mechanical performance of biodegradable polymers are well known to the polymer scientist, and include monomer selection, initiator selection, processing conditions, and the presence of additives. These factors in turn influence the polymer's hydrophilicity, crystallinity, melt and glass-transition temperatures, molecular weight, molecular-weight distribution, end groups, sequence distribution (random versus block), and presence of residual monomer or additives.

Biodegradation can be accomplished by synthesizing polymers that have hydrolytically unstable linkages in the backbone. The most common chemical functional groups with this characteristic are esters, anhydrides, orthoesters, and amides.

Technology for making the biodegradable implant generally falls into one of two categories: thermo-gelling (sol to gel) polymers that convert from liquid to solid or semi-solid when heated to body temperature, and solvent eluting polymeric compositions that solidify as solvent elutes from the composition into the body and the polymer becomes more concentrated.

A thermo-gelling composition is preferably liquid at room temperature (i.e. 20 or 25° C.), and a solid or gel at body temperature (i.e. 37° C.). A preferred thermo-gelling composition comprises a poloxamer. The term "poloxamer" refers to any of the group of polyoxyethylene-polyoxypropylene block copolymers known in the art. Poloxamers are also known by the trade name Pluronics™, and are nonionic block copolymers composed of a central hydrophobic chain of polyoxypropylene (polypropylene oxide) flanked by two hydrophilic chains of polyoxyethylene (polyethylene oxide). Because the lengths of the polymer blocks can be customized, many different poloxamers exist that have slightly different properties. These polymers are commonly named with the word Poloxamer followed by a number to indicate which polymer is being discussed (e.g. Poloxamer 407). The poloxamer can optionally be modified with, for example, a chain extender such as terephthaloyl chloride, to improve the stability of the gel and decrease its rate of degradation in vivo. See Ahn et al., POLYM. INT. 54:842-847 (2005). Different types of poloxamers can also be mixed to vary the properties of the material.

The compositions of the present invention are preferably based upon poloxamers having an ethylene oxide/n-propylene oxide block polymer structure, random or ordered. The ethylene oxide preferably is in molar excess to the n-propyl oxide, and the ratio of ethylene oxide to n-propyl oxide units is preferably from 1:1 to 3:1. In one embodiment the block copolymer has the following block polymer structure:

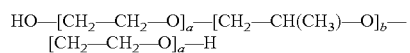

The ratio of a:b in the poloxamer is preferably from 1:1 to 3:1, more preferably from 1:5:1 to 2.5:1. The molecular weight of the copolymer is in one embodiment from 5000 to 25000, and is preferably from 9000 to 16000.

The liquid composition in one embodiment comprises from 10 to 25 weight parts of the poloxamer, and preferably comprises from 15 to 20 weight parts of the poloxamer. The liquid composition also comprises water, and in one embodiment the composition comprises 70 to 90 weight parts water, and in a preferred embodiment the composition comprises from 75 to 85 weight parts water.

The liquid also includes xanthan gum. In one embodiment from 1 to 3 weight parts of xanthan gum are present in the liquid. In a more preferred embodiment, from 1.5 to 2.5 weight parts are present.

The liquid can also be defined by several chemical characteristics, including a gel temperature that is between room temperature and 37° C.; a capacity to bioerode and elute said drug when implanted into mammalian tissue; and a capacity to adhere to mammalian tissue. In a particularly preferred embodiment, the implant is completely bioerodible, meaning that the entire formulation, once it has dissolved or disintegrated, can be processed via normal elimination pathways and excreted from the human body, optionally by the kidneys in the case of poloxamers.

The liquid in one embodiment has a viscosity at room temperature of from 100,000 to 1,000,000 cps, before being implanted and solidifying. In another embodiment, the viscosity of the liquid ranges from 200,000 to 500,000 cps. In addition, the liquid preferably comprises no component other than the above-described poloxamer and xanthan gum that materially changes the viscosity of said liquid at room temperature (i.e. by more than 100,000, 50,000 or 10,000 cps).

Other variables can also be modified in order to change the physical properties of the poloxamer. For example, FIG. 1 is taken from Ahn et al., POLYM. INT. 54:842-847 (2005), and reports a comparison in rates of erosion of various poloxamers, having the following chemical composition, wherein EG refers to ethylene glycol repeating units, PG refers to propylene glycol repeating units, and PH refers to terephthalic ester units.

TABLE I

| | Number average molecular weight (g/mol) | Polydispersity index | Number of repeating units |
|---|---|---|---|
| P85 | 4000 | 1.1 | $EG_{52}PG_{40}PH_0$ |
| F127 | 10000 | 1.2 | $EG_{200}PG_{65}PH_0$ |
| BMPII | 22000 | 1.9 | $EG_{286}PG_{220}PH_5$ |
| BMPIII | 31000 | 2.0 | $EG_{403}PG_{310}PH_7$ |

Figure 2:
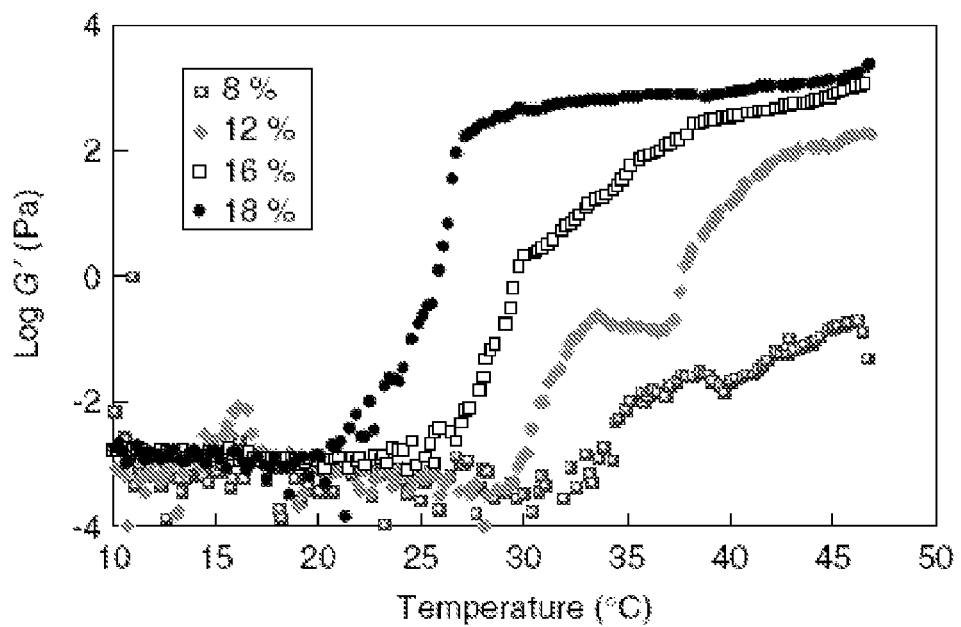
FIG. 2 illustrates the storage modulus (G') of a BMP aqueous solution as a function of temperature at different concentrations (wt %) of polymer (BMP III) in water, as described in POLYM. INT. 54:842-847 (2005). Heating rate was 0.2° C./min.

The dilution of the polymer in the solvent can also have a large impact on the properties of the poloxamer, including the temperature of gel conversion and the extent of conversion at a given temperature. For example, FIG. 2 is taken from Ahn et al., POLYM. INT. 54:842-847 (2005), and illustrates the storage modulus of a BMP aqueous solution as a function of temperature and poloxamer concentration.

Other suitable thermo-gelling polymers include PEG-PLGA-PEG triblock copolymers (Jeong et al. MACROMOLECULES (1999) 32(21):7064-7069), and PLGA-PEG-PLGA triblock copolymers (U.S. Pat. No. 6,004,573).

As noted above, the implant can also solidify through the action of solvent elution, so that the polymer solidifies as its concentration in the liquid increases. Polymers useful in solvent eluting polymeric compositions include polyglycolide (PGA), polylactide (PLA), poly(ε-caprolactone), poly(dioxanone) (a polyether-ester), and poly(lactide-co-glycolide). Using the polyglycolide and poly(l-lactide) properties as a starting point, it is possible to copolymerize the two monomers to extend the range of homopolymer properties. Glycolide may also be copolymerized with trimethylene carbonate (TMC), p-dioxanone, or a combination of TMC and p-dioxane, to form a suitably biodegradable implant.

Hydrophobic polymers that degrade by surface erosion rather than by hulk hydrolytic degradation can also be used in the process of the invention, especially when using drugs that are hydrolytically unstable. Two classes of these polymers are the polyanhydrides and the polyorthoesters. Polyanhydrides can be synthesized via the dehydration of diacid molecules by melt polycondensation, and their degradation times can be adjusted from days to years according to the degree of hydrophobicity of the monomer selected. Polyorthoesters also degrade by surface erosion, and degradation rates can be controlled by incorporation of acidic or basic excipients.

Any suitable biocompatible organic solvent can be employed to liquefy the composition, provided the biocompatible organic solvent is miscible to dispersible in aqueous medium or body fluid and can effectively dissolve the thermoplastic polyester. Suitable biocompatible organic solvents include, for example, N-methyl-2-pyrrolidone, 2-pyrrolidone, 2-ethoxyethanol, 2 ethoxyethyl acetate, ethyl acetate, ethyl lactate, ethyl butyrate, diethyl malonate, diethyl glutarate, tributyl citrate, acetyl-tri-n-hexylcitrate, diethyl succinate, 1 tributyrin, isopropyl myristate, propylene carbonate, dimethyl carbonate, ethylene glycol dimethyl ether, propylene glycol, 1,3-butylene glycol, caprolactone, N-dimethylformamide, dimethylacetamide, dimethyl sulfoxide, dimethyl sulfone, caprolactain, decylmethylsulfoxide, oleic acid, N,N-dimethyl-m-toluamide, 2,2 dimethyl-1,3-dioxolane-4-methanol, triacetin, ethyl acetate, benzyl alcohol, benzyl benzoate, solketal, glycofurol, dodecylazacycloheptan-2-one, or any combination thereof.

The suitable biocompatible organic solvent should be able to diffuse into body fluid so that the liquid implant coagulates or solidifies. It is also preferred that the biocompatible organic solvent for the biodegradable polymer be non-toxic and otherwise biocompatible.

The solubility of the biodegradable thermoplastic polyesters in the various biocompatible organic solvents will differ depending upon their crystallinity, their hydrophilicity, hydrogen-bonding, and molecular weight. Thus, not all of the biodegradable thermoplastic polyesters will be soluble in the same biocompatible organic solvent, but each biodegradable thermoplastic polymer or copolymer should have its appropriate biocompatible organic solvent. Lower molecular-weight polymers will normally dissolve more readily in the solvents than high molecular weight polymers. As a result, the concentration of a polymer dissolved in various solvents will differ depending upon type of polymer and its molecular weight. Conversely, the higher molecular-weight polymers will normally tend to coagulate or solidify faster than the very low-molecular-weight polymers. Moreover the higher molecular weight polymers will tend to give higher solution viscosities than the low molecular-weight materials.

A number of different types of drugs can be incorporated in the biodegradable implant, including analgesics, local anesthetics, antimicrobials, antibacterials, anti-inflammatories and anti-infectives. Therapeutically effective amounts of these drugs can be released at least about 8 hours after implanting, and up to about 30 days after implanting. In a preferred embodiment, a therapeutically effective amount of the drug is released up to about 5 or 15 days following implantation.

Analgesic drugs that can be incorporated into the dosage form include acetaminophen, ibuprofen, methylsalicylate, menthol, camphor, methylnicotinate, triethanolamine salicylate, glycol salicylate, or salicylamine.

Local anesthetics that can be incorporated into the dosage form include lidocaine hydrochloride, oxybuprocaine hydrochloride, procaine, benzocaine, xylocaine, etidocaine, cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, and mepivacaine.

Suitable antimicrobials include iodine, povidone iodine, benzalkonium chloride and chlorhexidine gluconate.

Suitable antibacterial drugs include the beta-lactam antibiotics, tetracyclines, chloramphenicol, clindamycin, neomycin, gramicidin, bacitracin, polymixin, sulfonamides, aminoglyco side antibiotics, tobramycin, nitrofurazone, nalidixic acid and analogs, and combinations thereof.

Suitable anti-inflammatories include cortisone, hydrocortisone, betamethasone, dexamethasone, fluocortolone, prednisolone, triamcinalone, indomethacine, sulindac and its salts and corresponding sulfide.

Suitable anti-infectives include bifonazole, siccanin, bisdequalinium acetate, clotrimazole, salicylic acid, sulfamethoxazole sodium, erythromycin and gentamicin sulfate.

The liquid may also contain one or more conventional pharmaceutical excipients selected from stabilizers, antioxidants, buffers and pH regulating agents.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Comparative Example 1

Comparative Evaluation of Prior Art Formulations

Figure 3:
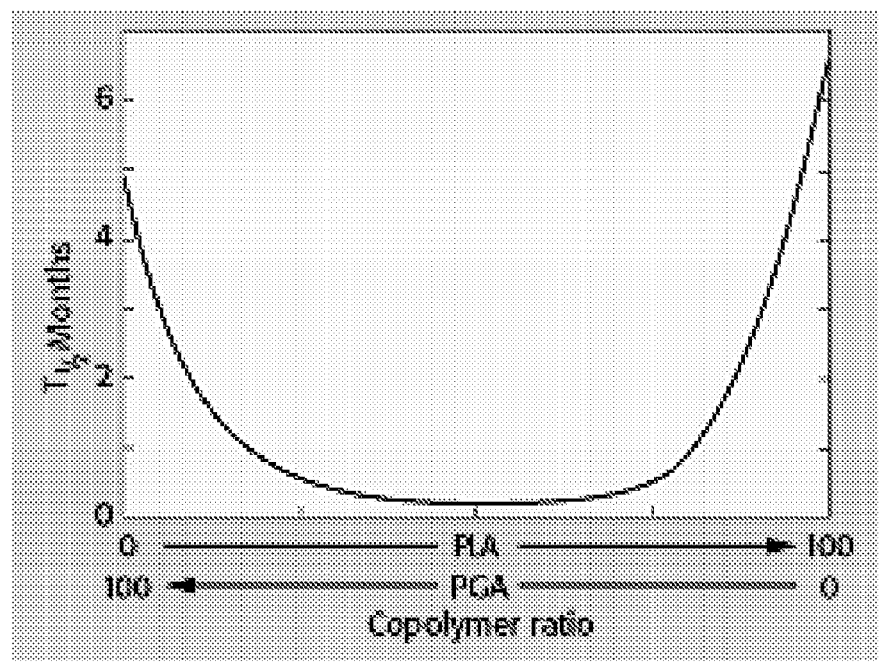
FIG. 3 presents the half-life of PLA and PGA homopolymers and copolymers when implanted into rat tissue, as taken from JOURNAL OF BIOMEDICAL MATERIALS RESEARCH, 11:711 (1977).

FIG. 1 presents a comparison of the erosion rates for poloxamers (P85 and F127) and BMPs of P85, wherein the initial concentration used to prepare the gel was 30%, as described in POLYM. INT. 54:842-847 (2005). FIG. 2 illustrates the storage modulus (G') of a BMP aqueous solution as a function of temperature at different concentrations (wt %) of polymer (BMP III) in water, as described in POLYM. INT. 54:842-847 (2005). The heating rate was 0.2° C./min. FIG. 3 presents the half-life of PLA and PGA homopolymers and copolymers when implanted into rat tissue, as taken from JOURNAL OF BIOMEDICAL MATERIALS RESEARCH, 11:711 (1977).

Example 1

Evaluation of Gelling Temperature in Different Poloxamers

The following compositions of poloxamers are provided as examples to demonstrate the effect on gelling temperature from various combinations of poloxamers.

TABLE A

| Formulation | Ingredients (w/w) | | | Gelling temperature |
| | F127 (%) | F108 (%) | F68 (%) | $T_{sol \rightarrow gel}$ (° C.) |
| --- | --- | --- | --- | --- |
| 1A | 20 | — | — | 19 |
| 1B | — | 20 | — | 30 |
| 1C | 20 | — | 2 | 25 |
| 1D | 5 | 15 | — | 30 |
| 1E | 11 | 10 | — | 26 |
| 1F | — | 20 | 2 | 36 |
| 1G | 17 | 2.5 | 3 | 31 |
| 1H | 10 | 10 | 5 | 37 |

Figure 4:
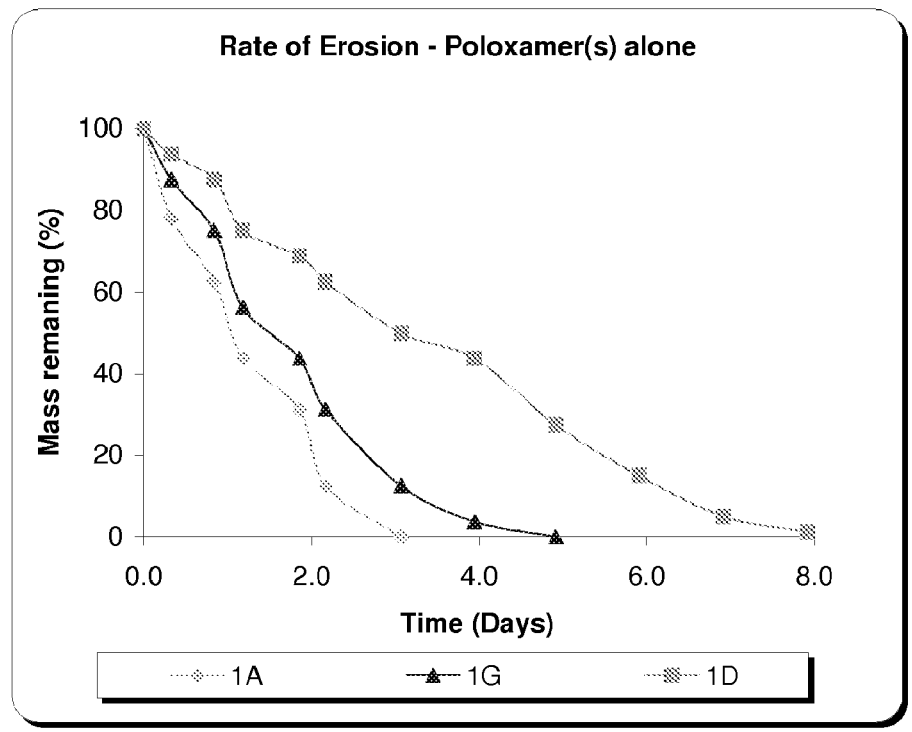
FIG. 4 plots the rate of erosion (percentage of mass remaining versus time in days) of three different poloxamer formulations, in which only the poloxamer was varied, as described more specifically in Example 1.

The erosion of matrices produced from the above-formulations was also studied and select results are presented in FIG. 4. The matrix consisting of a combination of poloxamers (F127 & F108) is retained for a maximum of 8 days, in vitro. This may not be sufficient for therapies such as antibiotics, where retention is required for a longer period (~7-15 days), in vivo. This warrants the addition of excipients, which reduce the erosion rate.

Example 2

Example 1a with Xanthan Gum

Figure 5:
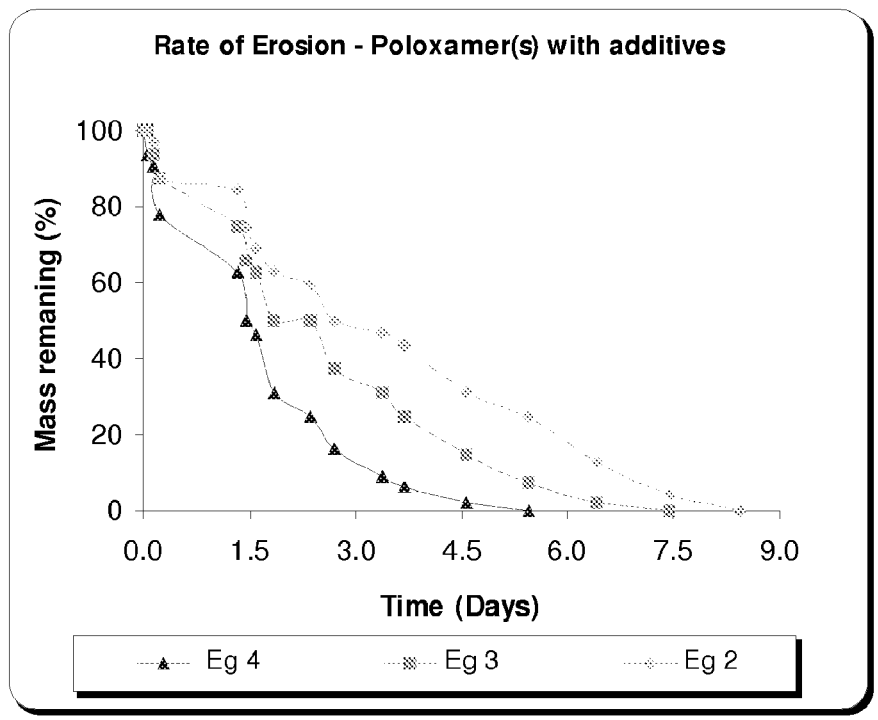
FIG. 5 plots the rate of erosion (percentage of mass remaining versus time in days) of three different poloxamer formulations, in which the sustained release excipient was varied, as described more specifically in Examples 2, 3 and 4.

In Examples 2-4, formulations 1A, 1D and 1G from Example 1 were combined with various excipients to demonstrate the effect of excipients on the gelling temperature and erosion rate. Erosion rates of the formulations reported in Examples 2-4 are plotted in FIG. 5.

TABLE B

| Formulation 2 | |
| --- | --- |
| Ingredients | Quantity [% (w/w)] |
| Clindamycin HCl | 1.00 |
| Poloxamer 407 (F127) | 16.50 |
| Xanthan gum | 0.50 |
| Water | 82.00 |
| Total volume | 100.00 |
| Gelling temperature (° C.) | 23 |

Example 3

Example 1D with Sodium Chloride

TABLE C

| Formulation 3 | |
| --- | --- |
| Ingredients | Quantity [% (w/w)] |
| Clindamycin HCl | 1.00 |
| Poloxamer 407 (F127) | 5.00 |
| Poloxamer 338 (F108) | 15.00 |
| Sodium Chloride | 0.50 |
| Water | 78.50 |
| Total volume | 100.00 |
| Gelling temperature (° C.) | 24 |

Example 4

Example 1G with Sodium Alginate

TABLE D

| Formulation 4 | |
|---|---|
| Ingredients | Quantity [% (w/w)] |
| Clindamycin HCl | 1.00 |
| Poloxamer 407 (F127) | 17.00 |
| Poloxamer 338 (F108) | 2.50 |
| Poloxamer 188 (F68) | 3.00 |
| Sodium alginate | 0.50 |
| Water | 76.00 |
| Total volume | 100.00 |
| Gelling temperature (° C.) | 27 |

These studies show that the excipients known in the art as "sustained-release" (SR) agents have varying effects. Different excipients were chosen to demonstrate the effect on the erosion rate, and the order would not change if the same excipients were chosen. The best from the above studies seems to be F127 with xanthan gum.

Example 5

Effect of Xanthan Gum on Erosion Rate

The following compositions of poloxamers with various percentages of xanthan gum were chosen to demonstrate the effect of xanthan gum on the erosion rate:

TABLE E

| | Quantity [% (w/w)] | | | |
|---|---|---|---|---|
| Ingredients | A | B | C | D |
| Clindamycin HCl | 1.00 | 1.00 | 1.00 | 1.00 |
| Poloxamer 407 (F127) | 16.50 | 16.50 | 16.50 | 16.50 |
| Xanthan gum | — | 0.50 | 1.50 | 2.00 |
| Water | 82.50 | 82.00 | 81.00 | 80.50 |
| Total volume | 100.00 | 100.00 | 100.00 | 100.00 |

Figure 6:
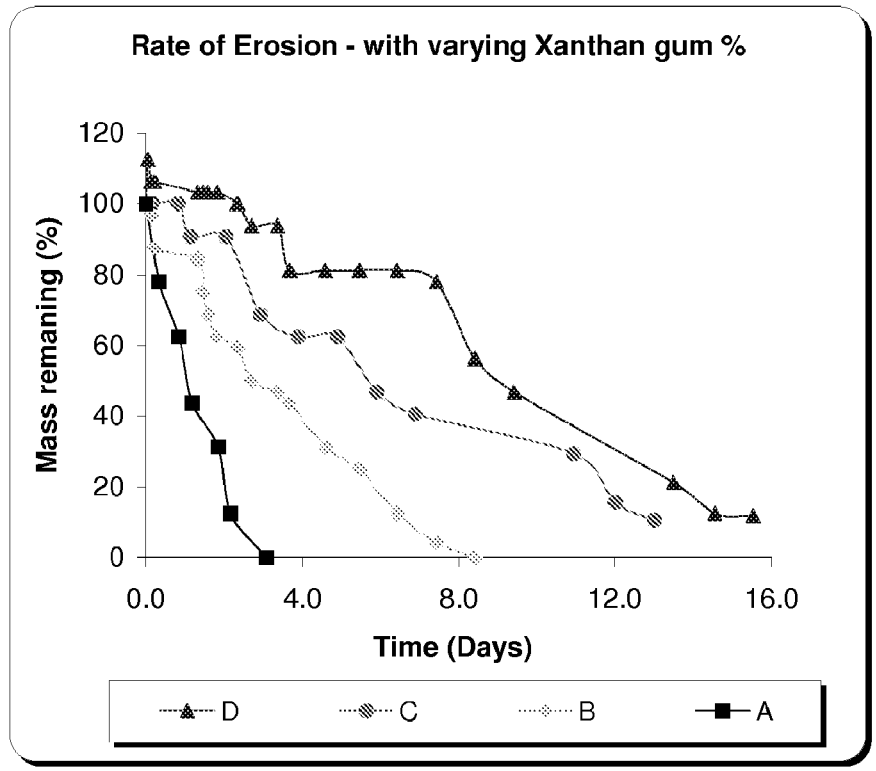
FIG. 6 plots the rate of erosion (percentage of mass remaining versus time in days) of four different poloxamer formulations, in which the percentage of xanthan gum was varied, as described more specifically in Example 5.

FIG. 6 plots the rate of erosion of formulations A-D. These studies show that xanthan gum, at percentages 1.5% and higher, produced the required duration for matrix retention.

Example 6

Effect of Xanthan Gum % on Bioadhesion

Figure 7:
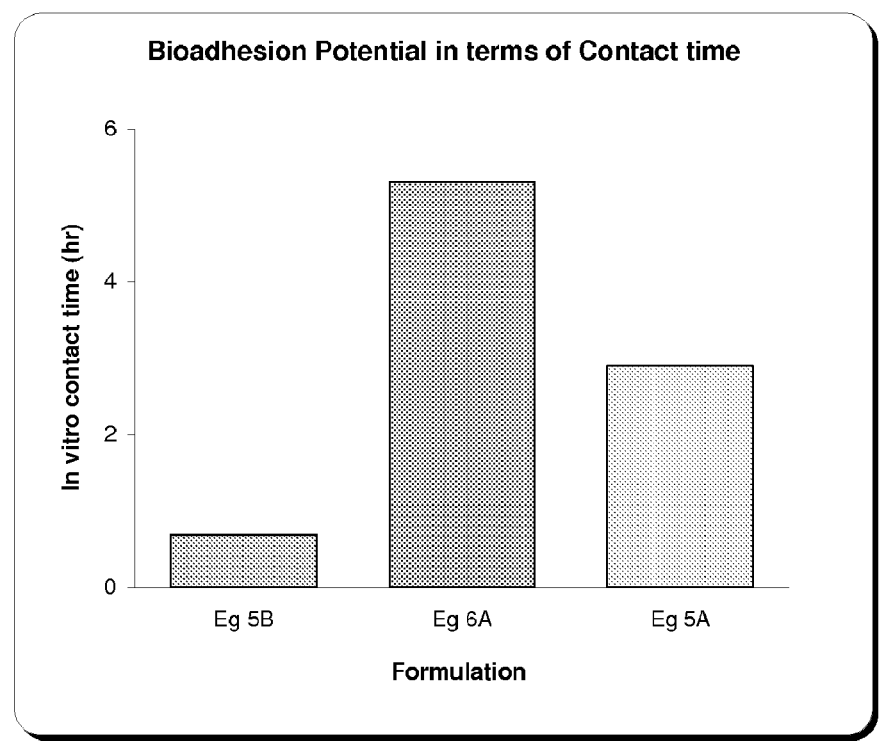
FIG. 7 is a bar chart describing the results of bioadhesion testing of three different formulations, as described in Example 6, in terms of time of adhesion, in which the percentage of xanthan gum in the formulations was varied.

The bioadhesive potential of various formulations was measured in terms of "contact time", an experiment wherein the same amount of a given formulation is applied to a steel disc of a specific weight. These discs are then placed on a glass plate uniformly coated with 10% gastric mucin and the same weight (352 g) is applied for the same time (20 min) to ensure adhesion. Then the plate is inverted and placed over a water bath maintained at 37° C. to simulate the moist condition that exists in the body. The time taken for the discs to detach is then recorded as the "contact time". The results of such a study is provided in FIG. 7, which shows that xanthan gum at 2% provides superior bioadhesive properties.

Formulation 6A had the following chemical composition:

TABLE F

| Ingredients | Quantity [% (w/w)] |
|---|---|
| Clindamycin HCl | 1.00 |
| Poloxamer 407 (F127) | 16.50 |
| Xanthan gum | 2.00 |
| Water (approx.) | 80.50 |
| Total | 100.00 |

Results of in vitro release testing showed that the incorporated drug was released over 9 days for formulations 6A compared to 3 days for formulation 5B.

The work presented in Examples 1-6 shows that xanthan gum can overcome the fragility of the poloxamer matrix, and provide sustained structure and release that are required for sustained-release drug delivery systems. Xanthan gum can be used in the 1-2% range to produce the required effect. Higher percentages could also be used, but would likely result in a product with high viscosity, which may be difficult to handle.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of delivering a drug to a bodily cavity in an animal comprising:
   a) providing a liquid that that comprises:
      i) from 70 to 90 weight parts water;
      ii) from 10 to 25 weight parts of a copolymer having the following block structure:

$$HO-[CH_2-CH_2-O]_a-[CH_2-CH(CH_3)-O]_b-[CH_2-CH_2-O]_a-H$$

wherein the ratio of a:b is from 1:1 to 3:1, and the molecular weight of said copolymer is from 9000 to 16000
      iii) from 0.5-3.0 weight parts of xanthan gum; and
      iv) a therapeutically effective amount of said drug;
   b) providing a body cavity in said animal; and
   c) forming a barrier against pathogen entry into said cavity by applying said liquid to said exposed tissue, whereupon said liquid gels in the form of an implant and adheres to said tissue around the entire periphery of said cavity.

2. The method of claim 1, wherein said liquid is characterized by a gel temperature that is between room temperature and the body temperature of said animal; a capacity to bioerode and elute said drug when implanted into said cavity; and a capacity to adhere to mammalian tissue.

3. The method of claim 1 wherein said liquid comprises from 75 to 85 weight parts water; from 15 to 20 weight parts of said copolymer; and from 1.5 to 2.5 weight parts of said xanthan gum.

4. The method of claim 1 wherein said liquid has a viscosity at room temperature of from 100,000 to 1,000,000 cps.

5. The method of claim 1 wherein said liquid contains no other component that changes the viscosity of said liquid at room temperature by more than 100,000 cps.

6. The method of claim 1, wherein said liquid comprises a therapeutically effective amount of an antibiotic.

7. The method of claim 1 wherein said liquid comprises a therapeutically effective amount of an anesthetic or a combination of anesthetics.

8. The method of claim 1, wherein said liquid comprises a therapeutically effective amount of an antibacterial agent.

9. The method of claim 1, wherein said liquid further comprises one or more conventional pharmaceutical excipients selected from stabilizers, antioxidants, buffers and pH regulating agents.

10. The method of claim 1, wherein said cavity is defined by the dental sulci, and said implant remains in the sulci for a period of from 5 to 21 days.

11. The method of claim 1, wherein said cavity is a surgical incision or wound, further comprising closing said surgical incision or wound.

12. The method of claim 1, wherein said liquid comprises an antibiotic, further comprising releasing a therapeutically effective amount of said antibiotic from said implant from 5 to 21 days.

13. The method of claim 1, wherein said liquid comprises an analgesic, further comprising releasing a therapeutically effective amount of said analgesic from said implant from 1 to 21 days.

14. A liquid composition comprising:
a) from 70 to 90 weight parts water;
b) from 10 to 25 weight parts of a copolymer having the following block structure:

wherein the ratio of a:b is from 1:1 to 3:1, and the molecular weight of said copolymer is from 9000 to 16000; and
c) from 0.5-3.0 weight parts of xanthan gum.

15. The composition of claim 14, characterized by a gel temperature that is between room temperature and 37° C.; a capacity to bioerode and elute said drug when implanted into mammalian tissue; and a capacity to adhere to mammalian tissue.

16. The composition of claim 14, comprising from 75 to 85 weight parts water; from 15 to 20 weight parts of said copolymer, and from 1.5 to 2.5 weight parts of said xanthan gum.

17. The composition of claim 14, wherein said liquid has a viscosity at room temperature of from 100,000 to 1,000,000 cps.

18. The composition of claim 14 comprising no other component that changes the viscosity of said liquid at room temperature by more than 100,000 cps.

19. The composition of claim 14, wherein said composition comprises a therapeutically effective amount of an antibiotic.

20. The composition of claim 14, wherein said composition comprises a therapeutically effective amount of an anesthetic.

21. The composition of claim 14, wherein said composition comprises a therapeutically effective amount of an antibacterial agent.

22. The composition of claim 14, further comprising one or more conventional pharmaceutical excipients selected from stabilizers, antioxidants, buffers and pH regulating agents.

* * * * *